United States Patent
Taylor et al.

(10) Patent No.: US 9,422,463 B2
(45) Date of Patent: *Aug. 23, 2016

(54) BUFFERED ADHESIVE COMPOSITIONS FOR SKIN-ADHERING MEDICAL PRODUCTS

(71) Applicant: HOLLISTER INCORPORATED, Libertyville, IL (US)

(72) Inventors: Michael Gerard Taylor, Mundelein, IL (US); Richard Iwao Murahata, Libertyville, IL (US)

(73) Assignee: HOLLISTER, INC., Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/463,912

(22) Filed: Aug. 20, 2014

(65) Prior Publication Data

US 2015/0045711 A1 Feb. 12, 2015

Related U.S. Application Data (63) Continuation-in-part of application No. 13/778,538, filed on Feb. 27, 2013.

(51) Int. Cl.
| | | |
|---|---|---|
| *A61L 26/00* | (2006.01) | |
| *A61L 28/00* | (2006.01) | |
| *C09J 123/20* | (2006.01) | |
| *C09J 133/02* | (2006.01) | |
| *A61F 13/02* | (2006.01) | |
| *A61L 15/58* | (2006.01) | |
| *A61L 24/04* | (2006.01) | |
| *A61L 24/06* | (2006.01) | |

(52) U.S. Cl.
CPC ............ *C09J 123/20* (2013.01); *A61F 13/0203* (2013.01); *A61F 13/0253* (2013.01); *A61L 15/58* (2013.01); *A61L 15/585* (2013.01); *A61L 24/043* (2013.01); *A61L 24/06* (2013.01); *C09J 133/02* (2013.01); *A61L 2400/14* (2013.01)

(58) Field of Classification Search
None
See application file for complete search history.

(56) References Cited

U.S. PATENT DOCUMENTS

| | | | | |
|---|---|---|---|---|
| 5,750,136 | A * | 5/1998 | Scholz et al. | 424/448 |
| 2003/0004451 | A1* | 1/2003 | Bark et al. | 602/53 |
| 2004/0156886 | A1* | 8/2004 | Kose | 424/449 |
| 2005/0215727 | A1* | 9/2005 | Feldstein et al. | 525/326.9 |
| 2007/0219287 | A1* | 9/2007 | Taylor | 523/111 |
| 2013/0316042 | A1* | 11/2013 | Guan et al. | 426/3 |

\* cited by examiner

*Primary Examiner* — Jeffrey Mullis
(74) *Attorney, Agent, or Firm* — Grogan, Tuccillo & Vanderleeden, LLP (57) ABSTRACT

Provided are buffered adhesive compositions comprising a high molecular weight non-neutralized polymeric acid and a high molecular weight partially neutralized polymeric acid and products such as wound dressings, ostomy skin barriers, and ostomy barrier rings incorporating the compositions.

11 Claims, 2 Drawing Sheets

BUFFERED ADHESIVE COMPOSITIONS FOR SKIN-ADHERING MEDICAL PRODUCTS

CROSS-REFERENCE TO RELATED APPLICATIONS

This application claims priority from U.S. provisional applications 61/604,663, filed Feb. 29, 2012, and 61/668,178, filed Jul. 5, 2012, and non-provisional application Ser. Nos. 13/778,538 and 13/778,497, both filed Feb. 27, 2013, and is a continuation-in-part of U.S. application Ser. No. 13/778,538, each of which is incorporated herein by reference in its entirety.

FIELD OF THE DISCLOSURE

This disclosure relates to the technical field of adhesive compositions for medical dressings and skin-adhering devices such as ostomy products, wound dressings, and other medical products intended to be adhesively secured to skin surfaces of users. The disclosure is specifically concerned with such adhesive compositions that contain a high molecular weight buffer and are capable of absorbing fluids and maintaining normal skin pH levels and to methods for making the compositions.

BACKGROUND

In a number of medical uses, a product is adhered directly to the skin, such as in the case of a wound dressing or an ostomy skin barrier or barrier ring. Such a product must be securely affixed to the skin to keep it in place and must absorb whatever fluid is produced under or near it, such as perspiration, wound exudate, fluid fecal matter, and the like. The product should also retain its structural integrity during use.

Wound dressings typically perform several functions to facilitate healing. These functions include absorbing wound exudate, regulating pH to create an optimal healing environment and reduce microbial activity, and protecting the wound from infection. Many such wound dressings are self-adhesive and contain an adhesive layer that typically adheres to the peri-wound skin of a wearer. It is known that skin often becomes irritated under wound dressings.

Known wound dressings achieve the aforementioned functionality through the use of several individual components. For example, known dressings often use hydrocolloids, e.g., carboxymethylcellulose (CMC), pectin, or gelatin, to absorb wound exudate. While some hydrocolloids are also capable of independently adjusting pH, the degree of pH buffering they can provide is limited by the amount of available hydrocolloid in the dressing, which, in turn, is dependent on the desired fluid handling properties of the dressing. Moreover, the buffering effect of hydrocolloids alone is not optimal.

Additionally, appropriate levels of absorption, pH control, and structural integrity are often difficult to achieve simultaneously. A certain extent of absorption by the wound dressing is required for pH control and is generally desirable in a wound dressing. However, the absorption of an excessive amount of fluid can cause an undesirable amount of swelling of the wound dressing, leading to distension and possible loss of adhesion. In certain instances, absorption of an excessive amount of fluid can cause dissolution of the adhesive composition, which is also highly undesirable.

Adhesive compositions containing hydrocolloids are well known, as disclosed, for example, in U.S. Pat. Nos. 5,571,080, 3,339,546, 4,192,785, 4,296,745, 4,367,732, 4,813,942, 4,231,369, 4,551,490, 4,296,745, 4,793,337, 4,738,257, 4,867,748, 5,059,169, and 7,767,291, the disclosures of which are incorporated herein by reference. Hydrocolloids are commonly used in what is commonly referred to as hydrocolloid skin barriers or hydrocolloid wound dressings. Such skin barriers and wound dressings normally include a water-insoluble pressure-sensitive adhesive as a continuous phase with particles of one or more hydrocolloids dispersed throughout the adhesive as a liquid-absorbing and swellable discontinuous phase.

The water-insoluble adhesive phase of commercial skin barriers and wound dressings typically consists of polyisobutylene (PIB), or block copolymers such as styrene-isoprene-styrene (SIS), or blends of these materials. The surface tack may be modified by the addition of tackifier components.

Patients with a permanent or temporary ostomy (colostomy, ileostomy, and the like) have need of a pouch to contain the expelled fecal material and urine. The pouch is normally attached to the peristomal skin with an adhesive skin barrier that attaches the pouch to the skin and absorb liquids flowing from the ostomy that are not contained by the pouch or fluids produced by the peristomal skin. A skin barrier is normally replaced every three to five days but may remain in place for up to a week. During use of the barrier, the peristomal skin may become irritated due to prolonged contact with the fecal material. Over time, the irritation can become severe. An ostomy appliance may also include a barrier ring in the immediate peristomal area to aid in sealing the appliance against the user's skin and to prevent leakage and/or further absorb fluids flowing from the ostomy.

In some applications, an ostomy skin barrier has an adhesive tape border around its periphery for additional security. The adhesive for said border is typically an acrylic adhesive. As used herein, the term "skin barrier" is intended to include any skin barrier either with or without an adhesive tape border.

Both wound exudate and fecal material contain proteolytic and lipolytic enzymes. These enzymes, when contained in a closed, moist environment, are thought to degrade the stratum corneum and contribute to the observed irritation of the skin around the wound or stoma. Moreover, since both wound dressings and ostomy skin barriers are normally removed and re-applied on a regular basis, the integrity of the skin under them becomes compromised and more susceptible to irritation than normal skin.

Normal skin has a so-called "acid mantle", which maintains the surface of the skin at a pH typically between about 4.0 and 5.5 (slightly acidic). This pH range promotes the growth of beneficial microorganisms and retards the growth of harmful microorganisms, while helping to maintain the integrity of the skin. At this pH level, the activity of (and hence the damage caused by) the proteolytic and lipolytic enzymes from wound exudate or fecal matter would not be severe. However, the wound exudate and stomal fluid normally have a pH in the range of 6.0 to 8.0. This increase in pH over the normal skin pH causes a significant increase in the activity of the enzymes and hence in their ability to cause irritation.

As with wound dressings, appropriate levels of absorption, pH control, and structural integrity are often difficult to achieve simultaneously for ostomy skin barriers and barrier rings. A certain extent of absorption by the skin barrier or barrier ring is required for pH control and is generally desirable. However, the absorption of an excessive amount of fluid can cause an undesirable amount of swelling of the skin barrier or barrier ring, leading to distension and possible loss of adhesion. In certain instances, absorption of an excessive amount of fluid can cause dissolution of the adhesive composition, which is also highly undesirable.

Current skin barriers incorporating hydrocolloids such as pectin and CMC have only limited pH buffering capacity. When exposed to water or saline solution, they are capable of adjusting pH to a level in the desired range from about 4.0 to 5.5. However, it is important to note that physiological fluids such as stoma output or wound exudates are also buffered, typically at pH levels close to neutral. When current skin barriers are exposed to such fluids, the strong buffering capacity inherent in the physiological fluid overwhelms the weak buffering capacity of the skin barrier. As a result, the pH at the surface of the skin barrier increases to approach the pH of the physiological fluid contacting the skin barrier. Thus, it would be desirable to provide a skin barrier with enhanced pH buffering capacity. It would also be desirable to provide a skin barrier with optimal absorption characteristics.

Similarly, current barrier rings incorporating hydrocolloids such as pectin and CMC have only limited buffering capacity. For the same reasons discussed above, it would be desirable to provide a barrier ring with optimal absorption characteristics.

An additional concern with an ostomy barrier ring is maintaining the structural integrity of the ring during use. In use, barrier rings are subject to erosion due to the effect of fluid flowing from the ostomy or produced by the peristomal skin. Since a skin barrier (including the barrier ring) may remain in place for up to a week, it is important that the barrier ring maintain its structural integrity throughout the expected use period while also having optimal absorption characteristics.

In view of the above, it would be desirable to have an adhesive composition containing a suitable buffer to maintain the pH of the skin under a wound dressing or a stomal skin barrier or the like product at about 4.0 to about 5.5 without being inherently irritating to the user's skin, and which would have an optimal extent of fluid absorption. It would also be desirable to have such a composition which could be used for a barrier ring that would (in addition to the above properties) maintain its structural integrity in use.

SUMMARY

In accordance with one aspect of the disclosure, a high molecular weight polymeric buffering adhesive composition is provided that is capable of optimal fluid absorption and pH buffering.

In accordance with another aspect of the disclosure, a wound dressing is provided that includes a high molecular weight polymeric buffer composition capable of optimal fluid absorption and pH buffering.

In accordance with another aspect of the disclosure, an ostomy skin barrier is provided that includes a high molecular weight polymeric buffer composition capable of optimal fluid absorption and pH buffering.

In accordance with another aspect of the disclosure, an ostomy barrier ring is provided that includes a high molecular weight polymeric buffer composition capable of optimal fluid absorption and pH buffering and which has resistance to erosion in use and thus optimal retention of its structural integrity.

In accordance with another aspect of the disclosure, a method is provided for using the high molecular weight polymeric buffer composition to manufacture a skin-adhering medical device, such as a wound dressing, ostomy skin barrier, or ostomy barrier ring.

An embodiment of the disclosure is a wound dressing that includes a flexible outer layer and a high molecular weight polymeric buffering adhesive composition applied to one side thereof, said adhesive providing pH buffering and optimal fluid absorption with minimal irritation to a wearer's skin.

Another embodiment of the disclosure is an ostomy skin barrier that includes a high molecular weight polymeric buffering adhesive composition applied to one side thereof, said adhesive composition providing pH buffering and optimal fluid absorption with minimal irritation to a wearer's skin.

Another embodiment of the disclosure is an ostomy barrier ring resistant to fluid erosion comprising a high molecular weight polymeric buffering adhesive composition, said adhesive composition providing pH buffering and optimal fluid absorption with minimal irritation to a wearer's skin and optimal retention of its structural integrity.

DESCRIPTION OF PREFERRED EMBODIMENTS

One embodiment of the present disclosure is directed to an adhesive composition comprising a high molecular weight buffer that absorbs fluids such as perspiration, wound exudate, and fecal matter, adjusts pH, and reduces enzymatic activity.

In particular, an embodiment of the present disclosure contemplates use of one or more high molecular weight polymers that are rich in acidic sites. Polymers with polyacid functionality can serve as buffers through the use of mixtures of their protonated and neutralized forms. Any high molecular weight polymer having pendant carboxyl groups that are capable of being partially neutralized is suitable for use in the present disclosure. Suitable polymers include, for example, polyacrylic acid and poly(2-alkyl acrylic acid) in which the alkyl chain is from one to five carbons in length and may be straight chain or branched chain. Poly methacrylic acid is the preferred poly (2-alkyl acrylic acid). Other suitable polymers are copolymers of any of acrylic acid and 2-alkyl acrylic acid monomers, copolymers of the foregoing monomers with maleic acid, olefinic polymers substituted with side chains containing free carboxylic acid groups, such as polyvinyl alcohol esterified with a diacid, triacid or polyacid (e.g., polyvinyl alcohol succinate), and the like.

As will be appreciated by one of skill in the relevant art, the buffering adhesive composition of the disclosure can employ one or more of any high molecular weight polymer having partially neutralizable pendant carboxyl groups that is capable of maintaining the pH of a test product at less than about 6.0 in the phosphate buffer challenge test described in Example 1.

A preferred embodiment of the present invention is a buffering adhesive composition that comprises at least two forms of high molecular weight polymer that are rich in acidic sites, one of which is in its non-neutralized form and the other of which is partially neutralized. The inventors have surprisingly discovered that the combination of non-neutralized and partially neutralized forms of the same or different high molecular weight polymer(s) rich in acidic sites permits independent modification of the extent of absorption and of pH control, a highly desirable quality in an adhesive composition for a medical device to be attached to a patient's skin, such as a wound dressing, an ostomy skin barrier, or an ostomy barrier ring.

The proportion of non-neutralized and partially neutralized polyacids, and the extent of neutralization of the partially neutralized polyacid are interrelated. The extent of neutralization of the partially neutralized polyacid may conveniently be from about 50% to about 100%, about 75% being preferred. Whatever extent of neutralization is selected, the proportion of non-neutralized and partially neutralized polyacid should be adjusted to achieve the desired pH range of between 4.0 and about 5.5 under the wound dressing or ostomy skin barrier. Those of ordinary skill in the adhesive formulation art can readily select an appropriate proportion of non-neutralized polyacid and partially neutralized polyacid for a given extent of neutralization of the partially neutralized polyacid to achieve the desired pH range.

The adhesive composition of the disclosure may also comprise a tackifier compound, such as a liquid PIB having a molecular weight such that it is below the entanglement molecular weight for PIB of about 8700 Daltons.

In a preferred embodiment, and for a partially neutralized cross linked polyacid that is about 75% neutralized, the non-neutralized form and the partially neutralized form of the high molecular weight polymeric acids may be present in a ratio of from about 4:1 to about 1:4 and preferably from about 3:1 to about 1:1. The two forms of the high molecular weight polymeric acids together may comprise from about 10 wt. % to about 25 wt. % of the entire adhesive composition, and preferably from about 15% to about 20% of the entire adhesive composition.

Polymers particularly well suited for use in an embodiment of the disclosure include polyacrylic acid (PAA) and polymethacrylic acid (PMA). Both PAA and PMA are available from, for example, Sigma-Aldrich Co., in a variety of forms, e.g., powder and solution, and in a range of molecular weights. Of the acrylic acid derivatives, PAA is preferred because it has the highest density of carboxylic acid sites per gram of compound and hence the highest extent of buffering per gram of compound. As used herein, "high molecular weight" PAA means greater than about 60,000 Daltons and as high as several million Daltons. The term has similar meanings for PMA and the other polymers described above.

One of ordinary skill in the art can readily determine the appropriate degree of neutralization for a particular polymer and use. Partial neutralization of PAA may be achieved by mixing PAA (plus water if appropriate) with a stoichiometrically appropriate amount of a strong base (e.g., NaOH) until the desired degree of neutralization is achieved. Other polymers may be treated similarly. Partially neutralized polyacids such as PAA are also available commercially.

PAA and related polymers exist in both cross-linked and non cross linked forms and the degree of cross-linking can be varied. The polymers used in the present disclosure are preferably cross-linked.

As stated, high molecular weight polymers, e.g., PAA and PMA, provide both effective pH buffering and absorption of fluids such as perspiration, wound exudate, or fecal matter. More specifically, the polymers function similarly to hydrocolloids such as pectin and CMC when dispersed within an adhesive matrix. That is, they absorb and swell and form viscous gels that provide mucoadhesion against a wearer's skin. As will be appreciated, the high molecular weight polymers may be the sole hydrocolloid component or, in other embodiments, they may be combined with other hydrocolloids, depending on the application and desired fluid handling capabilities of the wound dressing or skin barrier.

In one embodiment of the disclosure particularly useful for ostomy barriers, high molecular weight cross linked PAA and high molecular weight cross linked partially neutralized PAA are combined with polyisobutylene and either styrene-isoprene-styrene copolymer or polymer fibers (or both). In one such embodiment, the adhesive composition comprises cross linked high molecular weight PAA, cross linked high molecular weigh partially neutralized PAA, polyisobutylene, and styrene-isoprene-styrene block copolymer. In another such embodiment, the adhesive composition comprises cross linked high molecular weight PAA, cross linked high molecular weigh partially neutralized PAA, polyisobutylene, styrene-isoprene-styrene block copolymer and fibers such as cotton or preferably polyolefin such as polyethylene or polypropylene.

The adhesive component of the compositions of this disclosure may be any material that has pressure-sensitive adhesive properties with a strong affinity for the material of the fibers (if fibers are used). It may be a single pressure-sensitive adhesive or a combination of two or more pressure-sensitive adhesives. Adhesives useful in the present disclosure include, for example, those based on natural rubbers, synthetic rubbers, styrene block copolymers, polyvinyl ethers, poly(meth) acrylates (including both acrylates and methacrylates), polyolefins and silicones. A particular adhesive believed to be a preferred material of choice for this disclosure is a polyolefin, namely, polyisobutylene (PIB), but other pressure-sensitive adhesive materials having similar properties are believed suitable.

The fibers in the adhesive composition may be any fibrous material known in the art but preferably are compatible with, and even have a strong affinity for, the tacky adhesive component. It has been found that polyolefins such as polyethylene and polypropylene are highly compatible with PIB and are easily wetted by that adhesive medium. Both are non-polar saturated hydrocarbons.

In this embodiment, the PIB is preferably present as relatively high molecular weight PIB (molecular weight in the range of about 40,000 to 60,000 Dalton). For example, a skin barrier for ostomy use would normally contain 60,000 Dalton molecular weight PIB in the range of 50 wt. % to 65 wt. % or 40,000 Dalton molecular weight PIB in the range of 40 wt. % to about 55 wt. %. Additionally, combinations of 40,000 Dalton molecular weight and 60,000 molecular weight PIB may also be used, such as 32.5 wt. % 40,000 Dalton molecular weight PIB and 32.5 wt. % 60,000 Dalton molecular weight PIB.

Whatever materials are chosen for the buffering adhesive composition of the disclosure, it is highly desirable that the composition be at least minimally absorptive. The buffering capability of the present compositions is related in part to their absorptive capability. If no absorption were to occur, the high molecular weight polymeric buffer would not be contacted by the wound exudate or fecal material and hence would not be effective. Although compositions having lower absorptive capacity are included within the present disclosure, the compositions of the disclosure particularly useful for ostomy barriers should preferable have an absorptive capacity of at least about 0.15 $g/cm^2$ as measured in the test of Example 1. Additionally, the absorptive capacity of the buffering adhesive composition should preferably not exceed 0.60 $g/cm^2$. Since, as can be seen below, the absorptive capacity of the buffering adhesive composition can be adjusted by varying the proportion of the partially neutralized high molecular weight polymer relative to the non-neutralized high molecular weight polymer, one of skill in the art can readily adjust the absorptive capacity of the buffering adhesive composition to the desired level.

Preferred representative buffered adhesive compositions of the invention particularly useful for ostomy barriers include the following: 1) about 55.5 wt. % PIB, about 14.5 wt. % SIS, about 5% polyethylene fibers, about 15 wt. % cross linked polyacrylic acid, and about 10 wt. % partially neutralized cross linked polyacrylic acid; and 2) about 66 wt. % PIB, about 6.5 wt. % SIS, about 4% polyethylene fibers, about 14.5 wt. % cross linked polyacrylic acid, and about 9 wt. % partially neutralized cross linked polyacrylic acid. In the above compositions, the PIB preferably has a viscosity average molecular weight of 40,000 and the partially neutralized cross-linked polyacrylic acid is preferably about 75% neutralized.

In an embodiment of the disclosure particularly useful for ostomy barrier rings, high molecular weight cross linked PAA and high molecular weight cross linked partially neutralized PAA are combined with high molecular weight polyisobutylene (PIB), liquid PIB and polymer fibers.

The fibers in the adhesive composition may be any fibrous material known in the art but preferably are compatible with, and even have a strong affinity for, the tacky adhesive component. It has been found that polyolefins such as polyethylene and polypropylene are highly compatible with PIB and are easily wetted by that adhesive medium. Both are non-polar saturated hydrocarbons.

In this embodiment, the relative weight percentages of the high molecular weight PIB, liquid PIB, polymer fibers, high molecular weight cross linked PAA, and high molecular weight cross linked partially neutralized PAA should be chosen to optimize the fluid absorption and structural integrity of the composition. Generally speaking, the ability of the composition to absorb fluid and its ability to retain structural integrity are inversely related. That is, the more absorbent the composition is, the less its ability to retain its structural integrity, all other factors being constant. Surprisingly, the present inventors have discovered compositions which are able to simultaneously provide excellent absorption and structural integrity and are particularly well-suited for use in ostomy barrier rings. Preferably the compositions for barrier rings have an absorptive capacity of at least about 0.30 g/cm$^2$ as measured in the test of Example 3 and at least 50% of the composition remaining as measured in the 24 hour erosion resistance test of Example 3.

In this embodiment, preferably the high molecular weight PIB has a molecular weight in the range of about 40,000 to 60,000 Daltons and the liquid PIB has a molecular weight such that the PIB is a liquid at room temperature, typically in the range of about 1000 to about 8000 Daltons. The high molecular weight PIB may comprise either a single PIB having a molecular weight of about 40,000 to 60,000 Daltons or a mixture of PIBs with molecular weights in that range, such as a PIB with molecular weight of 40,000 Daltons and a PIB with a molecular weight of 60,000 Daltons. The liquid PIB preferably has a number average molecular weight of about 2800-3000 Daltons.

Buffered adhesive compositions of the invention particularly use for ostomy rings may have about 55-75 wt. % high molecular weight PIB, about 2.5-18 wt. % liquid PIB, about 2-8 wt. % polymer fibers, about 8-15 wt. % cross linked polyacrylic acid, and about 4-10 wt. % partially neutralized cross linked polyacrylic acid, provided that if the fiber content is less than 3 wt. %, the amount of cross linked polyacrylic acid is at least about 9.5% and the amount of liquid PIB is at least about 5 wt. %. Preferred such adhesive compositions may have about 60-75 wt. % high molecular weight PIB, about 2.5-7.5 wt. % liquid PIB, about 2-8 wt. % polymer fibers, about 8-15 wt. % cross linked polyacrylic acid, and about 4-10 wt. % partially neutralized cross linked polyacrylic acid, provided that if the fiber content is less than 3 wt. %, the amount of cross linked polyacrylic acid is at least about 9.5% and the amount of liquid PIB is at least about 5 wt. %. Other preferred such adhesive compositions may have about 62.5-72.5 wt. % high molecular weight PIB, about 5.5-7.5 wt. % liquid PIB, about 5-8 wt. % polymer fibers, about 10-14 wt. % cross linked polyacrylic acid, and about 4-7 wt. % partially neutralized cross linked polyacrylic acid. Still other preferred such adhesive compositions may have about 65-70 wt. % high molecular weight PIB, about 6.5-7.5 wt. % liquid PIB, about 6.5-7.5 wt. % polymer fibers, about 13-14 wt. % cross linked polyacrylic acid, and about 4.5-5.5 wt. % partially neutralized cross linked polyacrylic acid. Another preferred such adhesive composition has about 67 wt. % high molecular weight PIB, about 7 wt. % liquid PIB, about 7 wt. % polymer fibers, about 13.8 wt. % cross linked polyacrylic acid, and about 5.2 wt. % partially neutralized cross linked polyacrylic acid. In the above compositions, the partially neutralized cross-linked polyacrylic acid is preferably about 75% neutralized.

The following Examples describe the manufacture and testing of representative embodiments of the disclosure.

Test Samples:

Test samples were prepared by heat compression of barrier materials to a thickness of 0.020 inches and were laminated between a removable release liner and a flexible backing film.

Materials

High Molecular Weight Polyisobutylene (PIB)

Nippon Himol 4H with viscosity average molecular weight 40,000 Daltons produced by JX Nippon Oil and Energy Liquid Polyisobutylene (PIB)

Polyisobutylene TPC 1285 with a number average molecular weight of 2800 Daltons provided by Texas Petrochemicals Styrene-Isoprene-Styrene Block Copolymer (SIS)

Kraton™ D-1161P produced by Kraton Polymers

Polyolefin Fibers

Polyethylene Short Stuff Synthetic Pulp E380F supplied by MiniFIBERS, Inc.

Cross Linked Polyacrylic Acid

Carbopol® 980 NF provided by The Lubrizol Corporation.

Cross Linked Partially Neutralized Polyacrylic Acid

Aqua Keep™ 10 SH-PF provided by Sanyo Corporation of America.

pH Buffer Challenge:

A stock buffer solution (100 mM in Phosphate, 0.9% NaCl, pH 7.4) was prepared. Lower phosphate concentration buffers were prepared by dilution of the stock buffer with appropriate volumes of 0.9% NaCl. A 10 cm$^2$ surface of the barrier was exposed to 10 mL of buffer challenge solution.

Example 1

Adhesion Barrier Formulations

A series of formulations based on high molecular weight PIB, polyethylene fibers and partially neutralized polyacrylic acid (with two different molecular weights and two different degrees of neutralization) were prepared. Compositions were prepared using a Brabender Type REE6 mixer at 85° C. A 'masterbatch' containing 85% SIS and 15% PIB was prepared separately. The required weight of masterbatch was added to the mixer and was mixed at 36 rpm for 4 minutes. One-half the required amount of high molecular weight PIB was added and mixing was continued for 4 minutes. The required amounts of dry powders (PE fibers, Carbopol 980 NF and Aqua Keep 10 SH-PF) were pre-blended and then added to the mixer over a 4 minute period. The remaining one-half of the high molecular weight PIB ingredient was added and the mixing was continued for 10 minutes. The mixing chamber was sealed and vacuum was applied and mixing was continued for 15 minutes. Vacuum was released and the mixtures were removed from the mixer and allowed to equilibrate at room conditions before any testing was undertaken. Table 1 below shows compositions prepared in this fashion with weight percentages of the indicated ingredients along with testing results for these compositions.

Fluid Absorption and pH:

Fluid absorption was measured following the practice of standard EN 13726-1:2002 (Test methods for primary wound dressings—Part 1: Aspects of absorbency, Section 3.3). The hydrating fluid was normal saline (0.9% NaCl in water). The mass of fluid absorbed was measured by the weight gain in samples of 10 cm$^2$ surface area exposed to 20 mL normal saline. Samples were maintained in an oven (37° C., 15% relative humidity) for fixed time periods. Surface pH measurements were performed on samples following fluid absorption using a calibrated pH meter and a flat pH probe (Ross® model 8135BN).

responsible for the fluid absorption and pH properties. The ability to independently adjust absorption and pH properties would be advantageous since it would enable formulation of a range of barriers with different sets of properties. While acknowledging that the overall properties of the barriers are influenced by the relative amounts of all the ingredients, it has been surprisingly found that the partially neutralized cross linked high molecular weight polyacrylic acid component has the major influence on absorption and minimal influence on the pH properties while the non-neutralized cross linked high molecular weight polyacrylic acid component has the major influence on the pH properties and minimal influence on the absorption properties. These effects are shown by examining the correlations between product performance properties and ingredient levels for these two components. This is illustrated graphically by plotting the 24 hour fluid absorption results against ingredient levels for the two ingredients.

Figure 1:
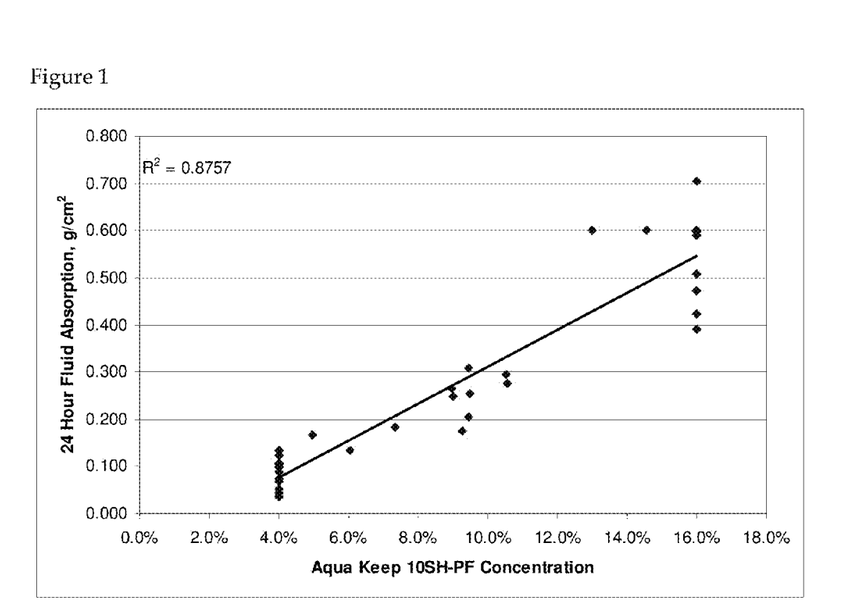
FIG. 1 is a graph showing the dependence of absorption on Aqua Keep 10 SH-PF concentration for the barrier of the invention.
Figure 2:
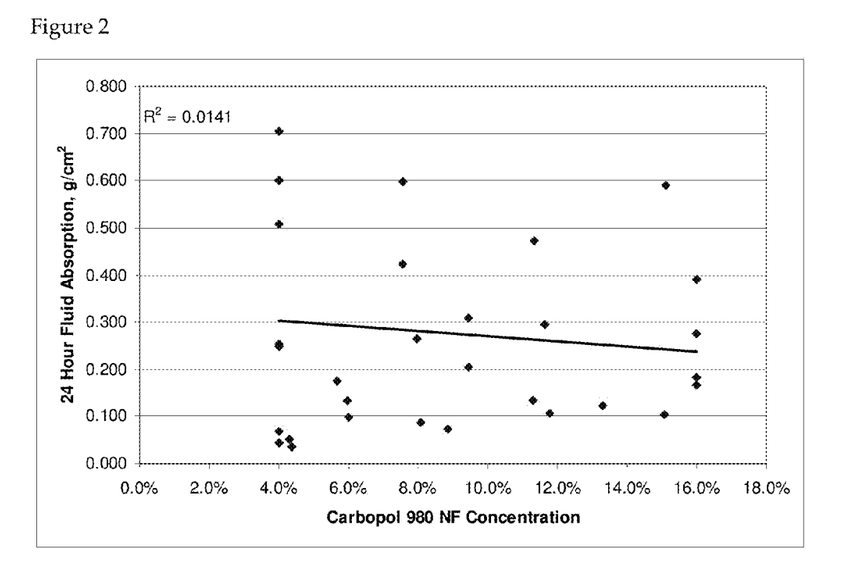
FIG. 2 is a graph showing the dependence of absorption on Carbopol 980 NF concentration for the barrier of the invention.

FIG. 1 illustrates the dependence of absorption on the Aqua Keep concentration for the full set of barriers. The straight line is the linear regression fit to the data. The $R^2$ value of 0.8757 means that more than 87% of the observed variation in measured fluid absorption is correlated with the variation in the Aqua Keep concentration. In contrast, there is essentially no correlation between fluid absorption and Carbopol concentration ($R^2=0.0141$) as illustrated in FIG. 2.

TABLE 1

| Nippon 4H PIB | Styrene-Isoprene-Styrene Copolymer | PE fibers | Carbopol 980 NF | Aqua Keep 10 SH-PF | 6 Hour Fluid Absorption | 6 Hour Surface pH | 24 Hour Surface pH | 24 Hour Fluid Absorption | 24 Hour Buffer Challenge Surface pH |
|---|---|---|---|---|---|---|---|---|---|
| 64.6% | 10.4% | 4.0% | 16.0% | 5.0% | 0.138 | 3.96 | 3.98 | 0.166 | 5.68 |
| 62.4% | 14.9% | 5.8% | 8.0% | 9.0% | 0.197 | 4.82 | 4.72 | 0.266 | 6.2 |
| 55.7% | 25.0% | 4.0% | 11.3% | 4.0% | 0.078 | 4.54 | 4.44 | 0.135 | 6.31 |
| 50.9% | 10.0% | 8.0% | 15.1% | 16.0% | 0.333 | 4.70 | 4.66 | 0.590 | 5.67 |
| 74.2% | 10.0% | 5.8% | 6.0% | 4.0% | 0.083 | 4.74 | 4.76 | 0.098 | 6.71 |
| 64.3% | 10.0% | 5.7% | 4.0% | 16.0% | 0.365 | 5.42 | 5.36 | 0.602 | 6.54 |
| 73.0% | 10.0% | 4.0% | 4.0% | 9.0% | 0.202 | 5.20 | 5.13 | 0.248 | 6.72 |
| 50.0% | 14.0% | 4.0% | 16.0% | 16.0% | 0.298 | 4.69 | 4.55 | 0.391 | 5.62 |
| 73.9% | 10.0% | 7.8% | 4.3% | 4.0% | 0.050 | 5.31 | 5.43 | 0.051 | 7.26 |
| 58.5% | 16.6% | 5.9% | 9.4% | 9.4% | 0.188 | 4.80 | 4.75 | 0.205 | 6.35 |
| 63.0% | 25.0% | 4.0% | 4.0% | 4.0% | 0.041 | 5.65 | 5.67 | 0.045 | 7.31 |
| 50.0% | 22.4% | 4.0% | 7.6% | 16.0% | 0.286 | 5.35 | 5.27 | 0.422 | 6.46 |
| 59.4% | 10.0% | 4.0% | 16.0% | 10.6% | 0.227 | 4.44 | 4.31 | 0.276 | 5.63 |
| 50.0% | 18.7% | 8.0% | 16.0% | 7.3% | 0.160 | 4.29 | 4.14 | 0.182 | 5.67 |
| 74.0% | 10.0% | 8.0% | 4.0% | 4.0% | 0.045 | 5.34 | 5.35 | 0.067 | 7.26 |
| 51.9% | 24.6% | 4.4% | 15.1% | 4.0% | 0.086 | 4.20 | 4.16 | 0.105 | 5.77 |
| 54.0% | 25.0% | 6.1% | 5.7% | 9.2% | 0.140 | 5.75 | 5.71 | 0.174 | 7.06 |
| 61.9% | 16.7% | 8.0% | 4.0% | 9.5% | 0.147 | 5.73 | 5.70 | 0.254 | 7.08 |
| 63.4% | 10.0% | 8.0% | 4.0% | 14.6% | 0.250 | 5.43 | 5.36 | 0.600 | 6.6 |
| 61.7% | 16.7% | 5.9% | 11.8% | 4.0% | 0.089 | 4.28 | 4.26 | 0.107 | 6.08 |
| 73.8% | 10.1% | 4.0% | 8.1% | 4.0% | 0.048 | 5.62 | 5.53 | 0.088 | 7.3 |
| 59.0% | 25.0% | 4.0% | 6.0% | 6.0% | 0.105 | 5.28 | 5.29 | 0.133 | 7.23 |
| 62.5% | 21.2% | 8.0% | 4.4% | 4.0% | 0.032 | 5.72 | 5.61 | 0.035 | 7.41 |
| 54.1% | 25.0% | 8.0% | 8.9% | 4.0% | 0.073 | 4.78 | 4.99 | 0.073 | 7.31 |
| 64.7% | 10.0% | 8.0% | 13.3% | 4.0% | 0.115 | 3.95 | 3.91 | 0.124 | 5.89 |
| 60.2% | 10.0% | 6.2% | 7.6% | 16.0% | 0.372 | 5.15 | 5.01 | 0.598 | 6.29 |
| 54.7% | 10.0% | 8.0% | 11.3% | 16.0% | 0.356 | 4.89 | 4.83 | 0.473 | 5.99 |
| 50.0% | 23.8% | 4.0% | 11.6% | 10.5% | 0.254 | 4.77 | 4.65 | 0.295 | 6.1 |
| 50.0% | 25.0% | 8.0% | 4.0% | 13.0% | 0.336 | 5.88 | 5.89 | 0.601 | 6.85 |
| 62.2% | 13.8% | 4.0% | 4.0% | 16.0% | 0.543 | 5.53 | 5.60 | 0.705 | 6.57 |
| 50.5% | 25.0% | 4.5% | 4.0% | 16.0% | 0.549 | 5.78 | 5.88 | 0.508 | 6.75 |
| 58.5% | 16.6% | 5.9% | 9.4% | 9.4% | 0.231 | 4.77 | 4.77 | 0.308 | 6.32 |

Figure 3:
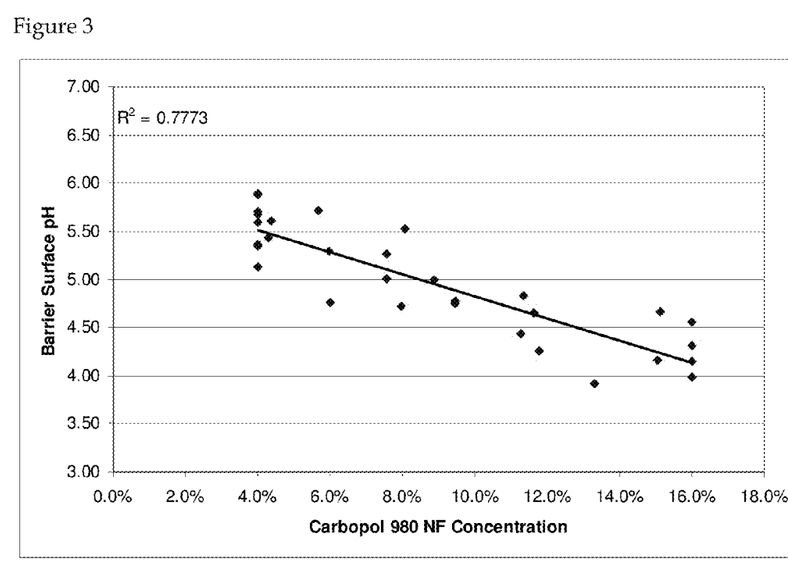
FIG. 3 is a graph showing the dependence of pH on Carbopol 980 NF concentration for the barrier of the invention.
Figure 4:
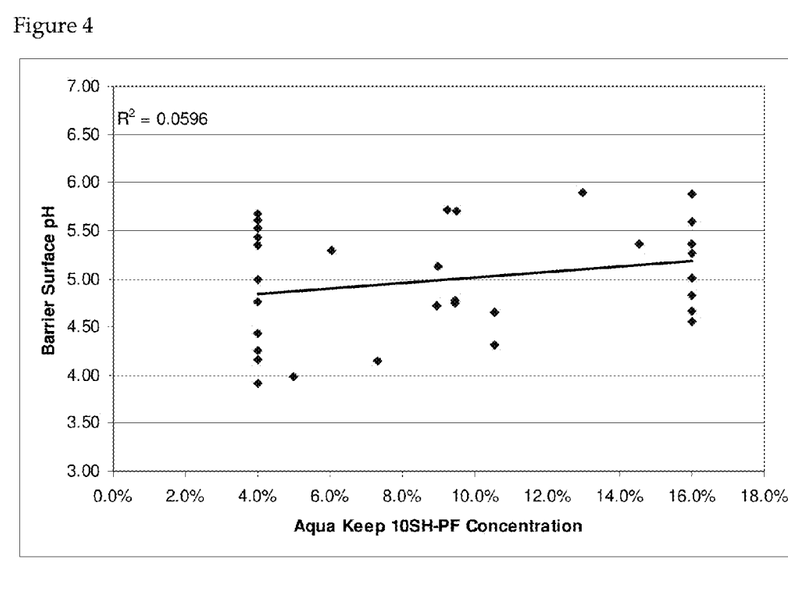
FIG. 4 is a graph showing the dependence of pH on Aqua Keep 10 SH-PF concentration for the barrier of the invention.

In order to meet user needs, it may be necessary to adjust the fluid absorption and pH control properties of the skin barriers. In the current formulations, the ingredient levels of the two polyacrylate components, the non-neutralized cross linked high molecular weight polyacrylic acid Carbopol 980 NF and the partially neutralized cross linked high molecular weight polyacrylic acid Aqua Keep 10 SH-PF are primarily In a similar fashion, FIGS. 3 and 4 illustrate that the pH of the barrier surface is strongly correlated with Carbopol 980 NF concentration (FIG. 3, $R^2=0.7773$) while there is essentially no correlation with Aqua Keep 10 SH-PF concentration (FIG. 4, $R^2=0.0596$).

High molecular weight polymers such as those set forth above provide both enhanced pH buffering capacity and absorption with reduced skin irritation. The inventors have surprisingly discovered that low molecular weight acids, such as citric acid, are unsuitable for buffer systems in the present disclosure. Although such low molecular weight acids function acceptably as buffers, low molecular weight acid buffer systems cause unacceptable irritation to the user's skin for use as contemplated herein. When a buffering adhesive composition similar to those of the disclosure but using a citric acid/citrate buffer instead of a high molecular weight polymer buffer was used in an adhesive dressing on human subjects, the subjects developed punctate ulcers under the dressing. The test results are shown below. Such an adhesive composition would be unsuitable for medical use. This result was both surprising and unexpected. The evaluation of a citric acid buffering system is described in Example 2 below.

Example 2

Irritation Testing

In 1968, Lanman et al. reported that several days of repeated exposures produced a method to discriminate among mildly irritating cosmetic type products. With modification including shorter time periods (e.g., 21 days) this method has remained the standard test for determining a product's potential for mild cutaneous irritation. The methodology involves 21 consecutive daily applications under occlusion. A 1% sodium lauryl sulfate (SLS) solution applied on a non-woven pad served as the positive control while preservative-free 0.9% sodium chloride applied in a similar manner served as the negative control. This standard test was used to assess the irritation potential of various barrier formulations applied directly to skin for 21 consecutive applications. Because the barrier materials are self-adhesive, it was possible to partially differentiate between the contribution from irritation due to mechanical properties (skin stripping) and chemical irritation, by comparing irritation resulting from direct application with that observed when the barrier was isolated from the skin using a non-woven pad moistened with sterile normal saline as well as using barriers constructed with and without buffering material.

A sufficient number of normal volunteer subjects was recruited to ensure completion with 30. Each subject was exposed to all test materials and the sites were randomized using a standard Latin Square design. Graders were blinded to the identity of the materials. Materials were reapplied to the same site for 21 consecutive days or until a discontinuation score was reached. The irritation data was treated using rank sum analysis. Rank sums range from 1 to 10 with higher numbers indicating more irritation.

Formulations used in the irritation test are described below:

| Citrate Barrier | |
|---|---|
| Oppanol ® B12 PIB (BASF) | 44.0% |
| TPC Group TPC1285 liquid PIB | 7.0% |
| Polyethylene Fiber | 3.5% |
| Pectin | 8.5% |
| Sodium Carboxymethyl Cellulose | 17.0% |
| Monosodium citrate Anhydrous | 16.0% |
| Trisodium Citrate Dihydrate | 4.0% |

| PAA Barrier | |
|---|---|
| Oppanol ® B12 PIB (BASF) | 55.0% |
| TPC Group TPC1285 liquid PIB | 8.7% |

-continued

| PAA Barrier | |
|---|---|
| Polyethylene Fiber | 4.4% |
| Partially neutralized PAA | 31.9% |

Using this standard methodology, the irritation potential of the formulation containing 20% citrate barrier (mean rank 9.59) was similar to that of the positive control (mean rank 9.27). Only the barrier formulation containing citrate caused irritation accompanied by focal erosions (punctate lesions), which was different from the more uniform irritation typically observed with exposure to SLS. The barrier formulated with PAA (mean rank 6.70) was significantly less irritating that either the positive control or the citrate buffer formulation. The slight irritation observed due to repeated exposure to the PAA barrier formulation was more uniform 'glazing' characteristic of repeated mechanical trauma, i.e., tape stripping. Both of these groups were different from the negative control (mean rank 2.68). The PAA buffer applied in petrolatum (31.8% PAA in petrolatum) was non-irritating, indicating a lack of inherent chemical irritation due to repeated exposure to PAA. This observation is consistent with the interpretation that the minor irritation observed with the barrier formulated with PAA is due to repeated mechanical damage.

Example 3

Example Formulations

Barrier Rings

A series of formulations based on high molecular weight PIB, Liquid PIB, polyethylene fibers, cross-linked polyacrylic acid and cross-linked partially neutralized polyacrylic acid was prepared. Example formulations were prepared using an AMK Type VI U 20 L mixer with a circulating oil heating jacket using a mixing blade rotational speed of 32 rpm. The total batch size for each example was 12.9 Kg.

The step-by-step mixing schedule was:
1. Heat mixer to 110° F.
2. Add Nippon 4H PIB and mix for 10 minutes
3. Add Aqua Keep 10 SH-PF and mix for 10 minutes
4. Stop the mixer and scrape down mixer sidewalls. Add ½ Carbopol 980 NF and mix for 10 minutes
5. Stop the mixer and scrape down mixer sidewalls. Add ½ Carbopol 980 NF and mix for 10 minutes
6. Stop the mixer and scrape down mixer sidewalls. Slowly add PE Fiber over 20 minutes through ¼" sieve
7. Stop the mixer and scrape down mixer sidewalls. Mix for 8 minutes
8. Stop the mixer and scrape down mixer sidewalls. Add Liquid PIB and mix for 8 minutes
9. Stop the mixer and scrape down mixer sidewalls. Mix for 16 minutes.
10. Stop the mixer and scrape down mixer sidewalls. Turn on Vacuum and mix for 32 minutes.

Vacuum was released and the mixtures were extruded from the mixer and allowed to equilibrate at room conditions before any testing was undertaken. Table 2 below shows compositions prepared in this fashion with weight percentages of the indicated ingredients along with testing results for these compositions.

Fluid Absorption and pH:

Fluid absorption was measured following the practice of standard EN 13726-1:2002 (Test methods for primary wound dressings—Part 1: Aspects of absorbency, Section 3.3). The hydrating fluid was normal saline (0.9% NaCl in water). The mass of fluid absorbed was measured by the weight gain in samples of 10 cm$^2$ surface area exposed to 20 mL normal saline. Samples were maintained in an oven (37° C., 15% relative humidity) for fixed time periods. Surface pH measurements were performed on samples following fluid absorption using a calibrated pH meter and a flat pH probe (Ross® model 8135BN).

Erosion Resistance:

Barrier ring samples (0.5 inch diameter circles) were weighed (W1). Saline solution (0.9% NaCl, 37° C.) was dripped onto the surface of the barrier ring samples continuously at a rate of 4 milliliters per minute for a fixed period. Following the saline exposure, samples were dried (65° C. for a minimum of 48 hours) and the dry samples were reweighed (W2). A value for Erosion Resistance (Percent Remaining) was calculated as: Percent Remaining=100*W2/W1. Favorable results in this in vitro erosion resistance test have been shown be correlated with favorable clinical results. Canadian Association for Enterostomal Therapy Annual Meeting, Ottawa, May 25-28, 2006; Poster: "Laboratory Measurements and User Appreciation of a Novel Ostomy Barrier Ring with Improved Wear Characteristics", M. G. Taylor, H. Geiger, M. R. Reimer, and R. I. Murahata.

Example 4

Irritation Testing

A sufficient number of normal volunteer subjects was recruited to ensure completion with 30. The subjects followed a 21-day exposure period for assessment of irritation. Twenty-one (21) repetitive and continuous patch applications of the test product and controls, to the same sites on the skin were made for approximately 24 hours exposure per application. Scoring occurred about 15 minutes after all patches had been removed on a subject. All scoring was completed prior to reapplication. Graders were blinded to the identity of the materials.

The test material was a representative embodiment of the disclosure comprising 67 wt. % high molecular weight PIB (Nippon Himol 4H), about 7 wt. % liquid PIB (TPC 1285), about 7 wt. % polyethylene fibers, about 13.8 wt. % cross linked polyacrylic acid (Carbopol 980 NF), and about 5.2 wt. % partially neutralized cross linked polyacrylic acid (Aqua Keep 10 SH-PF).

The test material was applied to the subject's skin in two presentations—either directly on the skin or overlaying a Webril pad pre-wetted with buffer enzyme solution. The enzyme solution was 50 mm phosphate, 0.9% NaCl pH 7.4 with added lipases and proteases. The controls were saline (negative), SLS (positive) and active enzyme pH 7.4 (positive). Five (5) sites on the back of each subject (approximately

TABLE 2

| Nippon 4H | Liquid PIB | PE fibers | Carbopol 980 | Aqua Keep 10SH | 6 Hour absorption g/cm$^2$ | 6 Hour pH | 24 Hour Buffer challenge pH | 24 Hour Erosion Resistance Percent Remaining |
|---|---|---|---|---|---|---|---|---|
| 67.2% | 7.5% | 4.4% | 10.9% | 10.0% | 0.444 | 4.49 | 5.76 | 79 |
| 75.0% | 2.5% | 6.0% | 10.5% | 6.0% | 0.319 | 4.18 | 5.64 | 104 |
| 61.5% | 7.5% | 6.0% | 15.0% | 10.0% | 0.505 | 4.29 | 5.66 | 80 |
| 72.5% | 7.5% | 2.0% | 8.0% | 10.0% | 0.204 | 4.78 | 5.9 | 42 |
| 75.0% | 7.5% | 2.0% | 9.5% | 6.0% | 0.423 | 4.32 | 5.58 | 66 |
| 66.3% | 7.5% | 5.2% | 15.0% | 6.0% | 0.328 | 3.97 | 5.22 | 49 |
| 66.3% | 7.5% | 5.2% | 15.0% | 6.0% | 0.234 | 3.96 | 5.23 | 55 |
| 73.5% | 2.5% | 6.0% | 8.0% | 10.0% | 0.552 | 4.8 | 5.92 | 99 |
| 61.5% | 7.5% | 6.0% | 15.0% | 10.0% | 0.462 | 4.27 | 5.62 | 67 |
| 67.7% | 2.5% | 5.2% | 15.0% | 9.6% | 0.54 | 4.27 | 5.68 | 44 |
| 75.0% | 2.5% | 6.0% | 10.5% | 6.0% | 0.324 | 4.22 | 5.6 | 102 |
| 68.3% | 5.5% | 6.0% | 12.2% | 8.0% | 0.483 | 4.3 | 5.62 | 88 |
| 75.0% | 7.5% | 2.0% | 9.5% | 6.0% | 0.357 | 4.32 | 5.67 | 67 |
| 72.5% | 7.5% | 2.0% | 8.0% | 10.0% | 0.191 | 4.76 | 5.94 | 40 |
| 68.0% | 6.2% | 5.1% | 11.5% | 9.1% | 0.584 | 4.41 | 5.67 | 82 |
| 72.5% | 7.5% | 6.0% | 8.0% | 6.0% | 0.311 | 4.43 | 5.92 | 103 |
| 75.0% | 5.0% | 4.0% | 8.0% | 8.0% | 0.487 | 4.64 | 5.86 | 99 |
| 72.5% | 7.5% | 6.0% | 8.0% | 6.0% | 0.323 | 4.45 | 5.87 | 100 |
| 68.0% | 6.2% | 5.1% | 11.5% | 9.1% | 0.493 | 4.35 | 5.69 | 77 |
| 68.3% | 5.5% | 6.0% | 12.2% | 8.0% | 0.388 | 4.31 | 5.67 | 84 |
| 68.0% | 6.2% | 5.1% | 11.5% | 9.1% | 0.493 | 4.35 | 5.75 | 81 |
| 75.0% | 5.0% | 4.0% | 8.0% | 8.0% | 0.402 | 4.58 | 5.93 | 100 |
| 73.5% | 2.5% | 6.0% | 8.0% | 10.0% | 0.518 | 4.72 | 5.96 | 98 |
| 67.2% | 7.5% | 4.4% | 10.9% | 10.0% | 0.524 | 4.53 | 5.77 | 74 |
| 68.0% | 6.2% | 5.1% | 11.5% | 9.1% | 0.511 | 4.45 | 5.72 | 71 |
| 67.7% | 2.5% | 5.2% | 15.0% | 9.6% | 0.519 | 4.24 | 5.66 | 54 |
| 67.00% | 6.00% | 6.00% | 15.00% | 6.00% | 0.238 | 3.98 | 5.28 | 40 |
| 65% | 7% | 5% | 16% | 6% | 0.425 | 4 | 5.51 | 34 |
| 63% | 10% | 6% | 15% | 6% | 0.454 | 4.07 | 5.59 | 70 |
| 60% | 19% | 8% | 16% | 6% | 0.4348 | 4.01 | 5.45 | 71 |
| 55% | 15% | 8% | 16% | 6% | 0.201 | 3.97 | 5.19 | 102 |
| 55.00% | 18.0% | 8.00% | 13.80% | 5.20% | 0.346 | 3.93 | 5.38 | 72 |
| 67.00% | 7.00% | 7.00% | 13.80% | 5% | 0.346 | 4 | 5.25 | 65 |

2 cm×2 cm) were utilized for the two presentations of the test material and the three controls.

The test material was minimally irritating, either when applied directly to the skin or when overlaying the pad wetted with buffer enzyme solution. In particular, the test material was able to mitigate the irritancy of the buffer enzyme solution to a level that was equivalent to saline. Only the positive controls (SLS and buffer enzyme solution pH 7.4 alone) caused significant irritation.

The study showed that the test material has the ability to provide buffering capacity against skin-active enzymes while being substantially non-irritating from chemical activity and repeated daily stripping.

An embodiment of the present disclosure contemplates the use of a high molecular weight polymeric buffer composition incorporated into the adhesive layer of a wound dressing. The wound dressing preferably includes a flexible outer layer such as a film. A hydrocolloid layer is on an inner side of the outer layer and contains the inventive high molecular weight polymeric buffer composition along with, optionally, an additional hydrocolloid such as CMC or pectin. As will be appreciated, the hydrocolloid layer is in direct contact with the wound bed.

In an embodiment, the wound dressing includes an adhesive component having a very high cohesive strength when hydrated to avoid potential disintegration of the dressing components in the wound bed. As will be appreciated, non-adhesive wound dressings incorporating the inventive buffer composition may also be possible.

A formulation suitable for a self-adhesive wound dressing would be, for example, formulation 8 in Table 1 which has high cohesive strength due to the relatively high SIS content along with high fluid absorption and buffering properties, useful for managing wound exudate. Those of ordinary skill in the art would know how to use this formulation in the preparation of a self-adhesive wound dressing.

Another embodiment of the present disclosure contemplates the use of a high molecular weight buffer composition incorporated into an ostomy skin barrier. The skin barrier may be permanently attached to an ostomy pouch (a "one step" or one piece arrangement) or may be separately attached using a flange clip system (a two piece arrangement). This embodiment of the disclosure will maintain the pH of the peristomal skin closer to the normal skin pH range of about 4.0 to about 5.5, thus reducing or eliminating the occurrence of irritation in the peristomal area.

Useful example formulations for ostomy skin barriers include those containing either polyethylene fibers or SIS. For example, formulation 13 of Table 1 combines desirable fluid handling ability with excellent pH control. Those of ordinary skill in the art would know how to use this formulation in the preparation of an ostomy skin barrier.

Useful example formulations for ostomy barrier rings include those described in Table 2. For example, formulation 34 of Table 2 combines desirable fluid handling ability with excellent pH control and structural integrity. Those of ordinary skill in the art would know how to use this formulation in the preparation of an ostomy barrier ring.

Also included in the present disclosure are methods of using the above-described high molecular weight polymeric buffer compositions. The compositions may be used to manufacture any skin-adhering device by applying to a side or surface of the device an amount of the composition effective to securely attach the device to the skin of the intended user.

While the invention has been described with reference to the preferred embodiments, it will be understood by those skilled in the art that various obvious changes may be made, and equivalents may be substituted for elements thereof, without departing from the essential scope of the present invention. Therefore, it is intended that the invention not be limited to the particular embodiments disclosed.

What is claimed is:

1. An adhesive composition for a skin-adhering medical device comprising a high molecular weight polymeric buffer composition which provides both pH buffering and fluid absorption, the composition comprising: about 55-75 wt. % high molecular weight PIB, about 2.5-18 wt. % liquid PIB, about 2-8 wt. % polymer fibers, about 8-15 wt. % cross linked high molecular weight polyacrylic acid, and about 4-10 wt. % cross-linked 75% neutralized high molecular polyacrylic acid, provided that if the fiber content is less than 3 wt. %, the amount of cross linked polyacrylic acid is at least about 9.5% and the amount of liquid PIB is at least about 5 wt. %.

2. The adhesive composition of claim 1 wherein the composition comprises about 60-75 wt. % high molecular weight PIB, about 2.5-7.5 wt. % liquid PIB, about 2-8 wt. % polymer fibers, about 8-15 wt. % cross linked high molecular weight polyacrylic acid, and about 4-10 wt. % cross-linked 75% neutralized high molecular polyacrylic acid, provided that if the fiber content is less than 3 wt. %, the amount of cross linked polyacrylic acid is at least about 9.5% and the amount of liquid PIB is at least about 5 wt. %.

3. An adhesive composition for a skin-adhering medical device comprising a high molecular weight polymeric buffer composition which provides both pH buffering and fluid absorption, the composition comprising: about 62.5-72.5 wt. % high molecular weight PIB, about 5.5-7.5 wt. % liquid PIB, about 5-8 wt. % polymer fibers, about 10-14 wt. % cross linked high molecular weight polyacrylic acid, and about 4-7 wt. % cross-linked 75% neutralized high molecular polyacrylic acid.

4. The adhesive composition of claim 3 wherein the composition comprises about 65-70 wt. % high molecular weight PIB, about 6.5-7.5 wt. % liquid PIB, about 6.5-7.5 wt. % polymer fibers, about 13-14 wt. % cross linked high molecular weight polyacrylic acid, and about 4.5-5.5 wt. % cross-linked 75% neutralized high molecular polyacrylic acid.

5. The adhesive composition of claim 3 wherein the composition comprises about 67 wt. % high molecular weight PIB, about 7 wt. % liquid PIB, about 7 wt. % polymer fibers, about 13.8 wt. % cross linked high molecular weight polyacrylic acid, and about 5.2 wt. % cross-linked 75% neutralized high molecular polyacrylic acid.

6. An ostomy barrier ring having an adhesive composition including a high molecular weight polymeric buffer, which provides pH buffering and fluid absorption, the composition comprising: about 55-75 wt. % high molecular weight PIB, about 2.5-18 wt. % liquid PIB, about 2-8 wt. % polymer fibers, about 8-15 wt. % cross linked high molecular weight polyacrylic acid, and about 4-10 wt. % cross-linked 75% neutralized high molecular polyacrylic acid, provided that if the fiber content is less than 3 wt. %, the amount of cross linked polyacrylic acid is at least about 9.5% and the amount of liquid PIB is at least about 5 wt. %.

7. The ostomy barrier ring of claim 6 wherein the adhesive composition comprises about 60-75 wt. % high molecular weight PIB, about 2.5-7.5 wt. % liquid PIB, about 2-8 wt. % polymer fibers, about 8-15 wt. % cross linked high molecular weight polyacrylic acid, and about 4-10 wt. % cross-linked 75% neutralized high molecular polyacrylic acid, provided that if the fiber content is less than 3 wt. %, the amount of cross linked polyacrylic acid is at least about 9.5% and the amount of liquid PIB is at least about 5 wt. %.

8. An ostomy barrier ring having an adhesive composition including a high molecular weight polymeric buffer, which provides pH buffering and fluid absorption, the composition comprising: about 62.5-72.5 wt. % high molecular weight PIB, about 5.5-7.5 wt. % liquid PIB, about 5-8 wt. % polymer fibers, about 10-14 wt. % cross linked high molecular weight polyacrylic acid, and about 4-7 wt. % cross-linked 75% neutralized high molecular polyacrylic acid.

9. The ostomy barrier ring of claim 8 wherein the adhesive composition comprises about 65-70 wt. % high molecular weight PIB, about 6.5-7.5 wt. % liquid PIB, about 6.5-7.5 wt. % polymer fibers, about 13-14 wt. % cross linked high molecular weight polyacrylic acid, and about 4.5-5.5 wt. % cross-linked 75% neutralized high molecular polyacrylic acid.

10. The ostomy barrier ring of claim 8 wherein the adhesive composition comprises about 67 wt. % high molecular weight PIB, about 7 wt. % liquid PIB, about 7 wt. % polymer fibers, about 13.8 wt. % cross linked high molecular weight polyacrylic acid, and about 5.2 wt. % cross-linked 75% neutralized high molecular polyacrylic acid.

11. A wound dressing that includes a flexible outer layer; and a high molecular weight polymeric buffering adhesive composition applied to a side of the flexible outer layer, the adhesive composition providing pH buffering and fluid absorption, the adhesive composition comprising: about 55-75 wt. % high molecular weight PIB, about 2.5-18 wt. % liquid PIB, about 2-8 wt. % polymer fibers, about 8-15 wt. % cross linked high molecular weight polyacrylic acid, and about 4-10 wt. % cross-linked 75% neutralized high molecular polyacrylic acid, provided that if the fiber content is less than 3 wt. %, the amount of cross linked polyacrylic acid is at least about 9.5% and the amount of liquid PIB is at least about 5 wt. %.

* * * * *